(12) United States Patent
Mateu et al.

(10) Patent No.: US 8,021,674 B2
(45) Date of Patent: Sep. 20, 2011

(54) COSMETIC GEL PRODUCT ON THE BASIS OF OILS AND GELLING AGENTS

(75) Inventors: Juan Mateu, Oak Ridge, NJ (US); Guang Yu Cheng, Neshanic Sta., NJ (US); Domnica Cernasov, Ringwood, NJ (US); Ralph Macchio, Sparta, NJ (US); Blanca Pallarca, Bayonne, NJ (US)

(73) Assignee: Coty B.V., CC Haarlem (NL)

( * ) Notice: Subject to any disclaimer, the term of this patent is extended or adjusted under 35 U.S.C. 154(b) by 1132 days.

(21) Appl. No.: 10/461,657

(22) Filed: Jun. 13, 2003

(65) Prior Publication Data

US 2004/0018219 A1    Jan. 29, 2004

(30) Foreign Application Priority Data

Jun. 14, 2002 (DE) ................................. 102 27 409

(51) Int. Cl.
*A61K 8/18* (2006.01)
(52) U.S. Cl. .......................................... 424/401; 424/64
(58) Field of Classification Search ............... 424/401
See application file for complete search history.

(56) References Cited

U.S. PATENT DOCUMENTS

| | | | |
|---|---|---|---|
| 4,822,602 A * | 4/1989 | Sabatelli | 424/65 |
| 4,948,578 A * | 8/1990 | Burger et al. | 424/68 |
| 5,633,286 A | 5/1997 | Chen | |
| 5,650,144 A | 7/1997 | Hofrichter et al. | |
| 5,756,028 A | 5/1998 | Liao | |
| 5,798,111 A * | 8/1998 | Kanga et al. | 424/401 |
| 6,139,824 A * | 10/2000 | Ribery et al. | 424/65 |
| 6,375,938 B1 * | 4/2002 | Clothier et al. | 424/65 |
| 6,403,070 B1 | 6/2002 | Pataut et al. | |
| 2002/0055562 A1 | 5/2002 | Butuc | |

FOREIGN PATENT DOCUMENTS

| | | |
|---|---|---|
| WO | WO 93/23008 | * 11/1993 |
| WO | WO 95/30405 A | 11/1995 |
| WO | WO 98/27953 A | 7/1998 |
| WO | WO 00/26285 A | 5/2000 |
| WO | WO 02/17870 A | 3/2002 |

* cited by examiner

*Primary Examiner* — Jake M. Vu
(74) *Attorney, Agent, or Firm* — Novak Druce + Quigg LLP

(57) ABSTRACT

The invention refers to a new cosmetic gel product which contains oils or fats and suitable gel forming polymers and which has improved characteristics as regards stability and structure. The product of the invention comprises 5-85% by weight of a fat phase forming agent selected from among oils, hydrogenated hydrocarbons, alkenes, mono esters, di esters, tri esters and mixtures thereof, 0.1-15% by weight of a further gelling agent selected from among 12-hydroxy stearic acid, polyethylene whose molecular weight is between 400 and 2500 Daltons, glyceryl behenate and mixtures thereof, 0.5-5% by weight of a surface-active agent, and ad 100% by weight other auxiliary substances, carrier substances, active substances and mixtures thereof, all percentages being relative to the weight of the gel product. The product is wax-free and free of fatty absorbing substances and has as a stick a water content up to 60% and with no sweating or bleeding.

11 Claims, No Drawings

COSMETIC GEL PRODUCT ON THE BASIS OF OILS AND GELLING AGENTS

BACKGROUND OF THE INVENTION

1. Field of the Invention

The invention refers to a new cosmetic gel product which contains oils or fats and suitable gel forming agents and which has improved characteristics as regards stability and structure.

2. Description of the Related Art

WO 00/26285 discloses gelled esters, oils and fats which contain one or more diblock copolymer(s), triblock copolymer(s), star polymer(s), radial polymer(s) as gelling agent for the fats, oils and/or esters. The gels obtained are thick liquids, soft to semi-solid gels and contain approximately 0.1 to 10% by weight of the said gelling agents in the case of diblock copolymers and 0.1 to 40% by weight of same in the case of triblock copolymers. Mixtures of diblock and triblock copolymers, which in combination with esters are marketed as ester gels, contain approximately 75-98% by weight of esters and 2-25% by weight of polymeric gelling agent. Hydrocarbon gels contain 80-99% by weight of hydrocarbons and 1-20% by weight of polymeric gelling agent.

U.S. Pat. No. 5,558,872 discloses di- and triblock copolymers mixed with mineral oil (Geahlene®) which, adding a fatty acid modifier, such as a fatty acid ester such as isopropyl myristate, and a silicone oil, are processed into skin protection products for people suffering from incontinence. U.S. Pat. No. 5,888,492 describes a skin conditioning composition consisting of di- and triblock co-polymers, a mineral oil, a fatty acid ester and non-ionic surface-active agents.

SUMMERY OF THE INVENTION

The object of the invention is to provide a new cosmetic gel product which, on the basis of known oils and gelling agents, improves the characteristics of the gel as regards stability and in addition brings about substantial improvements as regards structure.

According to the invention, the gel product comprises 5 to 85% by weight of a fat phase forming agent selected from among oils, hydrogenated hydrocarbons, alkenes, mono esters, di esters, tri esters and mixtures thereof, 0.1 to 15% by weight of a gelling agent selected from among 12-hydroxy stearic acid, poly-ethylene whose molecular weight is between 400 and 2500 Daltons, glyceryl behenate and mixtures thereof, 0.5 to 5% by weight of a surface-active agent, and wherein the gel product is free of waxes and fatty absorbing substances and all percentages being relative to the weight of the gel product, and wherein the gel product is transparent or translucent solid stick.

The gel product further comprises other auxiliary substances, carrier substances, active substances and mixtures thereof to 100% by weight, where all percentages being relative to the weight of the gel product, For the invention used oils can be usual cosmetic oils such as mineral oil, hydrogenated hydrocarbons, hydrogenated polyisobutene, squalane from synthetic or natural sources, cosmetic esters or ethers, which can be branched or unbranched, saturated or unsaturated, vegetable oils, or mixtures of two or more thereof.

Especially suitable oils are, for example, silicone oils, mineral oils, hydrogenated polyisobutene, polyisoprene, squalane, tridecyltrimellitate, trimethylpropane triisostearate, isodecylcitrate, neopentyl glycol diheptanoate, PPG-15-stearyl ether, calendula oil, jojoba oil, avocado oil, macadamia nut oil, castor oil, cocoa butter, coconut oil, corn oil, cotton seed oil, olive oil, palm kernel oil, rapeseed oil, safflower seed oil, sesame seed oil, soybean oil, sunflower seed oil, wheat germ oil, grape kernel oil, kukui nut oil, thistle oil, and mixtures thereof.

Suitable esters or ethers are, for example, (INCI names): dipentaerythrityl hexacaprylate/hexacaprate/tridecyl trimellitate/tridecyl stearate/neopentyl glycol dicaprylate dicaprate, propylene glycol dioctanoate 5, propylene glycol dicaprylate 2,30 dicaprate, tridecyl stearate/neopentyl glycol dicaprylate dicaprate/tridecyl trimellitate, neopentyl glycol dioctanoate, isopropyl myristate, diisopropyl dimer dilinoleate, trimethylpropane triisostearate, myristyl ether, stearyl ether, cetearyl octanoate, butyl ether, dicaprylyl ether, PPG1-PEG9 lauroyl glycol ether, PPG15 stearyl ether, PPG14 butyl ether, Fomblin HC25.

A content of 3 to 50% by weight of an ethylene-/propylene/styrene copolymer or a butylene/ethylene/styrene co-polymer or a mixture thereof is possible in an embodiment of the invention as other gel oil forming agents for the oil or fat phase. Such a mixture comprises different copolymer contents, depending on the oil, fat or ester which is to gel, such as polybutene, isohexadecane etc. Commercially available products which are particularly preferred are Versagel® ME 750, ME 1600, MC 1600, MP 500/750/1600, ML 500/750/1600, ME 500/750/1600 and similar ones of Penreco, Karms City, Pa., USA (MP=isopropyl palmitate; ME=polybutene; ML=alkyl benzoate).

Preferably, the oil, fat or ester components which can form a gel with the copolymers are contained in a range of 20 to 60% by weight.

The further gelling agent is preferably contained in the range of 1 to 15% by weight, particularly 3-12% by weight, in the case of 12-hydroxy stearic acid; 1 to 15% by weight, particularly 2 to 11% by weight, in the case of polyethylene whose molecular weight is between 400 and 2500; and 1 to 10% by weight in the case of glyceryl behenate. In addition, mixtures of high-molecular polyethylene with 12-hydroxy stearic acid, each in the range of 3-10% by weight relative to the weight of the overall composition, particularly in a ratio of 1:1, are particularly preferred.

Polyethylenes whose molecular weight is in the range of 450 to 800 Daltons are particularly preferred.

Anionic, amphoteric, non-ionic or cationic surface-active agents or mixtures thereof can be used as surface-active agents. Non-ionic surface-active agents are particularly preferred.

Suitable non-ionic surfactants include, are not limited to, coconut acyl mono or diethanol amides, alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol, or silicone-based such as cetyl dimethicone copolyol and others. Mixtures of any of the foregoing surface active agents may also be used.

A preferred range for the use of these preferred agents is 1 to 4% by weight, particularly 1 to 3% by weight.

The inventive preparation contains also cosmetic auxiliary and carrier substances as they are used conventionally in such compositions, for example, water, preservatives, colorings, fillers, pigments with coloring effect, thickeners, fragrances, alcohols, polyols, electrolytes, emulsifiers, stabilizers.

Additional cosmetic active agents which can be used include e.g. inorganic and organic sunscreens, scavengers, moisturizing substances, vitamins, enzymes, vegetable active agents, polymers, melanine, antioxidants, anti-inflammatory natural active agents, disintegration products of yeast or plant substances prepared by gentle ultrasonic treatment according to WO94/137983, kaolin as well as kaolin modified with SiO$_2$ according to WO94/17588.

Antioxidants include vitamins such as vitamin C and derivatives thereof, for example, ascorbic acetate, ascorbic phosphate, and ascorbic palmitate; vitamin A and derivatives thereof; folic acid and derivatives thereof; vitamin E and derivatives thereof, such as tocopheryl acetate; flavones or flavonoids; amino acids, such as histidine, glycine, tyrosine, tryptophan, and derivatives thereof; carotenoids and carotenes such as, for example, α-carotene, β-carotene; uric acid and derivatives thereof; α-hydroxy acids such as citric acid, lactic acid, malic acid; stilbene and derivatives thereof etc.

Polyols, which are also possible ingredients of the gel of the invention, are e.g. propylene glycol, dipropylene glycol, ethylene glycol, isoprene glycol, glycerin, sorbitol and mixtures thereof. The share of the polyol is in the range of 0.1 to 40% by weight, preferably from about 5% to about 20% by weight of the gel composition.

When the product of the present invention contains additionally emollients, the emollients can be normally provided in the form of a plurality of compounds, such as stearyl alcohol, glyceryl mono ricinoleate, glyceryl mono stearate, propane-1,2-diol, butane-1,3-diol, cetyl alcohol, isopropyl isostearate, stearic acid, isobutyl palmitate, oleyl alcohol, isopropyl laurate, decyl oleate, octadecane-2-ol, isocetyl alcohol, cetyl palmitate, silicone oils such as dimethylpolysiloxane, isopropyl myristate, isopropyl palmitate, polyethylene glycol, lanolin, cocoa butter, vegetable oils such as corn oil, cotton seed oil, olive oil, mineral oils, butyl myristate, palmitic acid etc.

It is moreover advantageous to add to the compositions according to the invention corresponding water and/or oil soluble UVA or UVB filters or both. Advantageous oil-soluble UVB filters include 4-amino benzoic acid derivatives such as 4-(dimethylamino)-benzoic acid-(2-ethylhexyl) ester; esters of cinnamic acid such as 4-methoxy cinnamic acid (2-ethylhexyl) ester, benzophenone derivatives such as 2-hydroxy-4-methoxy benzophenone; 3-benzylidene camphor derivatives such as 3-benzylidene camphor.

Preferred oil-soluble UV filters are benzophenone-3, butyl-methoxybenzoylmethane, octyl methoxycinnamate, octyl salicylate, 4-methylbenzylidene camphor, homosalate and octyl dimethyl PABA.

Water-soluble UVB filters are, for example, sulfonic acid derivatives of benzophenone or of 3-benzylidene camphor or salts, such as Na or K salts, of 2-phenyl benzimidazole-5-sulfonic acid.

Pigments, pigment mixtures or powders with a pigment-like effect, also including those with a pearl-gloss effect, may be included in the gel and comprises e.g. iron oxides, aluminum silicates such as ochre, titanium (di)oxide, mica, kaolin, calcium carbonate, French chalk, mica-titanium oxide, mica-titanium oxide-iron oxide, bismuth oxychloride, expanded and non-expanded synthetic polymer powders, powdery natural organic compounds such as milled solid algae, milled plant parts and mica-titanium oxide-organic dye and all organic colorants, pigments and dyes.

According to the invention, the product contains no wax, but in a special embodiment of the invention it is present in a solid form, e.g. in the form of a self-supporting stick the melting point of which is above 48° C., especially >50° C.

According to another special embodiment of the invention, the product contains 10 to 60% by weight of water, particularly 30 to 50% by weight of water and especially 30-40% of water, and the product is present in the form of a stick having an excellent stability, which was able to be convincingly demonstrated by means of tests. No sweating or melting can be observed in such a stick. In the same way, no sweating or bleeding (exudation of additives from the product surface) and no melting when brought into contact with the warm skin of the user, which in general results in an undesirable deformation of the product at the point of contact, can be observed in a water- and wax-free stick which contains 50-60% by weight of a fat phase (ester, hydrocarbon or Silicone) and is composed according to the invention. The melting point is above 50° C. in this case too. In addition, a shiny, comfortable, non-dry film on the skin, e.g. on the lips, is achieved. This is particularly surprising since most lipsticks are matt and form a very dry film on the lips which has to be wetted several times in order to become shiny. The moisturizing properties of similar products are clearly exceeded although no additional moisturizing substances are contained.

According to another embodiment of the invention, the composition according to the invention in the form of a gelled paste can contain 40 to 50% by weight of water without this affecting the stability of the product. Such a wax-free product also has a softer structure than the state-of-the-art products which do contain wax.

According to another embodiment of the invention are the esters selected from the group consisting of diisopropyl adipate, isopropyl palmitate, diisopropyl maleate, diisopropyl dimer dilinoleate, isostearyl isostearate, isostearyl dimer dilinoleate and mixtures thereof.

It is preferred that fat phase forming agent is a mixture of at least two alkenes and two esters, such as disclosed in the examples.

In a further preferred embodiment of the invention the gel product is an anhydrous stick containing (in % by weight)

| | |
|---|---|
| 12-Hydroxy stearic acid | 0.3-8 |
| Polyethylene (Mw 450-1000) | 0.1-9 |
| Preservative | 0.1-0.5 |
| ABIL ® EM 90 Polysiloxane (Cetyl PEG/PPG-10/1 Dimethicone) | 0.5-6 |
| Polydecene (200-800 D)(New Phase Nexbase 2004 fg, 2006 fg and 2008 fg | 0.1-10 |
| Isopropyl Palmitate | 1-30 |
| Colorants | 0.1-30 |
| Filler | 1-20 |
| Phenyl Trimethicone | 1-20 |
| Polybutene | 0.1-60 |
| Diisopropyl Adipate | 0.1-60 |

Especially the product contains 10-50% by weight polybutene and 8-20% by weight diisopropyl adipate.

In a further preferred embodiment of the invention the gel product is a water gel stick containing

| | |
|---|---|
| 12-Hydroxy stearic acid | 0.1-9 |
| Polybutene | 0.1-19 |
| Polyethylene (Mw 450-2000) | 0.1-10 |
| Glyceryl Stearate | 0.1-4 |
| Preservative | 0.1-0.8 |
| ABIL ® EM 90 Polysiloxane (Cetyl PEG/PPG-10/1 Dimethicone) | 0.5-6 |
| Polydecene (200-800 D) | 0.1-10 |
| Phenyl Trimethicone | 1-20 |
| Diisostearyl Maleate | 2-10 |
| Colorants | 2-10 |
| Filler | 1-20 |
| Water | 0.1-60 |
| Diisopropyl Dimer Dilinoleate | 1-15 |

The cosmetic gel products according to the invention cannot only be processed into soft and semi-solid gels as could be expected for the known copolymers by those skilled in the art, but, in combination with the additional gel forming agents, result in very strong and stable products which are highly resistant to melting and bleeding. These characteristics remain unchanged notwithstanding a high variability of the carrier substances in the fat phase as regards both the type and amount of same. It is particularly surprising that, while maintaining its advantageous characteristics, the product can have a very high water content of up to 50% by weight and form a shiny, non-dry, highly comfortable and long-lasting film. This enables 3 in 1 products to be manufactured which do as well as stand-alone products when applied onto all parts of the face including eyes and lips.

Foundations can be manufactured in the same way.

The film formed on the skin is very unobtrusive and therefore makes the gel products according to the invention suitable for covering wrinkles, concealing imperfections and similar applications.

The use of the cosmetic preparations according to the invention, for example, can be realized in the form of sun screen creams, sun screen gels, after sun products, day creams, night creams, masques, body lotions, body gels, cleansing lotions, body powder, eye cosmetics, deep conditioning hair treatments, hair rinses, hair shampoos, shower gels, shower oils, bath oils as well as in the form of decorative cosmetics such as makeup, lipsticks, nail polish, mascara etc. The manufacture of such products is carried out in a way known to a person skilled in the art.

The product of the invention contains no fatty absorbing substances such as e.g. talcs, starches, clays, silicas, polyolefins, polystyrenes, teflons, ceramic beads etc.

In the following, the invention shall be described in detail by examples. All percent figures are by weight if not other set out.

EXAMPLE 1

Anhydrous Stick I

| | |
|---|---|
| 12-Hydroxy stearic acid | 7 |
| Polyethylene (Mw 450-1000) | 8 |
| Preservative | 0.3 |
| ABIL ® EM 90 Polysiloxane (Cetyl PEG/PPG-10/1 Dimethicone) | 4.0 |
| Polydecene (200-800 D)(New Phase Nexbase 2004 fg, 2006 fg and 2008 fg | 5.0 |
| Isopropyl Palmitate | 12 |
| Colorants | 10 |
| Filler | 5 |
| Phenyl Trimethicone | 4 |
| Polybutene | ad 100 |
| Diisopropyl Adipate | 12 |

The oil phase is heated to 90° C. during stirring. After that the oil phase is cooled to 75° C. and colorants, preservatives and actives are added all while mixing at 800-1500 rpm. The stick is poured at 70° C.

EXAMPLE 2

Water Gel Stick

| | |
|---|---|
| 12-Hydroxy stearic acid | 4 |
| Polybutene | 19 |
| Polyethylene (Mw 450-2000) | 8 |
| Glyceryl Stearate | 2 |
| Preservative | 0.6 |
| ABIL ® EM 90 Polysiloxane (Cetyl PEG/PPG-10/1 Dimethicone) | 2 |
| Polydecene (200-800 D) | 10 |
| Phenyl Trimethicone | 7 |
| Diisostearyl Maleate | 8 |
| Colorants | 7 |
| Filler | 2.4 |
| Water | ad 100 |
| Diisopropyl Dimer Dilinoleate | 10 |

The water is heated to 75° C. and than mixed to the separate prepared oil phase. Further see example 1.

EXAMPLE 3

Anhydrous Stick II

| | |
|---|---|
| 12-Hydroxy stearic acid | 5.5 |
| Polydecene | 30 |
| Polybutene | 20.7 |
| Preservative | 0.3 |
| Polyethylene Mw 200-500 | 1.1 |
| Colorants | 1 |
| Diisostearyl Dimer Dilinoleate | 18 |
| Isostearyl Isostearate | 23 |

The preparation is according example 1.

EXAMPLES 4 AND 5 (COMPARATIVE EXAMPLES)

Stability tests were carried out in which 20 test objects in the form of sticks were stored in a climate-controlled room at a temperature of 50° C. and a relative air humidity of 55%. The test objects were composed according to Example 2 (for Example 4) and according to Example 1 (for Example 5).

Every two weeks, an inspection was carried out. After 8 weeks, no sweating was able to be observed in the sticks according to Example 4 nor in those according to Example 5. Neither could any bleeding be observed in any test object of the two types of sticks.

EXAMPLE 6 (COMPARATIVE EXAMPLE)

In tests carried out using test persons who were asked to evaluate the product with regard to 15 different aspects during the test phase, the overall evaluation of compositions according to Example 4 was as follows (in % of the test persons):

| | |
|---|---|
| fair: | 18% |
| good: | 12% |
| very good: | 24% |
| excellent: | 44% |

The moisturizing effect of e.g. gelled mineral oil (Versagel) was assessed to be 50% above that of pure mineral oil while at the same time there were further improvements, such as e.g. regarding lip conditioning, water-proofness, etc.

The invention claimed is:

1. A cosmetic gel product on the basis of oils and gelling agents which product comprises:

| | |
|---|---|
| 12-Hydroxy stearic acid | 0.1-9 wt-% |
| Polybutene | 0.1-19 wt-% |
| Polyethylene (Mw 450-2000) | 0.1-10 wt-% |
| Glyceryl Stearate | 0.1-4 wt-% |
| Preservative | 0.1-0.8 wt-% |
| Cetyl PEG/PPG-10/1 Dimethicone | 0.5-6 wt-% |
| Polydecene (200-800 D) | 0.1-10 wt-% |
| Phenyl Trimethicone | 1-20 wt-% |
| Diisostearyl Maleate | 2-10 wt-% |
| Colorants | 2-10 wt-% |
| Filler | 1-20 wt-% |
| Water | 0.1-60 wt-% |
| Diisopropyl Dimer Dilinoleate | 1-15 wt-% | wherein the gel product is free of additional fatty absorbing substances and the gel product is a transparent or translucent solid water gel stick.

2. A cosmetic gel product which is a lipstick comprising:
5 to 85% by weight of a fat phase forming agent comprising a mixture of: i) at least two alkenes selected from the group consisting of: polybutene, polydecene, hydrogenated polyisobutene and squalene, and, ii) at least two esters selected from the group consisting of: diisostearyl dimer dilinoleate, diisopropyl adipate, isopropyl palmitate, diisopropyl maleate, diisostearyl maleate, diisopropyl dimer dilinoleate, isostearyl isostearate, and isostearyl dimer dilinoleate,
0.1 to 15% by weight of gelling agents, said gelling agents consisting of a mixture consisting of 12-hydroxy stearic acid and polyethylene having a molecular weight between 400 and 2500 Daltons,
10 to 60% by weight of water, and
0.5 to 5% by weight of a surface-active agent,
wherein the cosmetic gel product is a lipstick free of additional fatty absorbing substances and all percentages being relative to the weight of the gel product, wherein the remaining to 100% by weight are other auxiliary substances, carrier substances and active substances, and
wherein said other auxiliary and carrier substances are selected from the group consisting of water, preservatives, colorings, fillers, pigments with coloring effect, fragrances, alcohols, polyols, electrolytes, emulsifiers, stabilizers and combinations thereof.

3. The cosmetic gel product of claim 1, wherein the cosmetic gel product which is a lipstick is a transparent or translucent solid stick.

4. The cosmetic gel product of claim 3, wherein the cosmetic gel product which is a lipstick is a solid stick containing 30 to 50% by weight of water.

5. The cosmetic gel product of claim 4, wherein the cosmetic gel product which is a lipstick has a melting point of >48° C.

6. The cosmetic gel product of claim 5, wherein the cosmetic gel product which is a lipstick has a melting point of >50° C.

7. The cosmetic gel product of claim 1, wherein the polyethylene has a molecular weight in the range of 400 to 1000 Daltons.

8. A cosmetic gel product which is a lipstick, comprising:
5 to 85% by weight of a fat phase forming agent comprising a mixture of: i) at least two alkenes selected from the group consisting of: polybutene, polydecene, hydrogenated polyisobutene and squalene, and ii) at least two esters selected from the group consisting of: diisostearyl dirtier dilinoleate, diisopropyl adipate, isopropyl palmitate, diisopropyl maleate, diisostearyl maleate, diisopropyl dimer dilinoleate, isostearyl isostearate, and isostearyl dimer dilinoleate,
0.1 to 15% by weight of gelling agents, said gelling agents consisting of a mixture consisting of 12-hydroxy stearic acid and polyethylene having a molecular weight between 400 and 2500 Daltons,
10 to 60% by weight of water, and
0.5 to 5% by weight of a surface-active agent,
wherein the cosmetic gel product is a lipstick free of additional fatty absorbing substances and all percentages being relative to the weight of the gel product, wherein the fatty absorbing substances are selected from the group consisting of talcs, starches, clays, silicas, polyolefins, polystyrenes, teflons, ceramic beads, and mixtures thereof, wherein the remaining to 100% by weight are other auxiliary substances, carrier substances and active substances, and
wherein said other auxiliary and carrier substances are selected from the group consisting of water, preservatives, colorings, fillers, pigments with coloring effect, fragrances, alcohols, polyols, electrolytes, emulsifiers, stabilizers and combinations thereof.

9. The cosmetic gel product of claim 2, wherein said active substances are selected from the group consisting of inorganic and organic sunscreens, scavengers, moisturizing substances, vitamins, enzymes, vegetable active agents, polymers, melanine, antioxidants, anti-inflammatory natural active agents, disintegration products of yeast or plant substances prepared by gentle ultrasonic treatment, kaolin, kaolin modified with $SiO_2$, and combinations thereof.

10. The cosmetic gel product of claim 8, wherein said active substances are selected from the group consisting of inorganic and organic sunscreens, scavengers, moisturizing substances, vitamins, enzymes, vegetable active agents, polymers, melanine, antioxidants, anti-inflammatory natural active agents, disintegration products of yeast or plant substances prepared by gentle ultrasonic treatment, kaolin, kaolin modified with $SiO_2$, and combinations thereof.

11. The cosmetic gel product of claim 2, wherein the cosmetic gel product which is a lipstick comprises pigments with coloring effect.

* * * * *